Feb. 12, 1974 F. W. ANDERSON Plant Pat. 3,477
NECTARINE TREE
Filed Oct. 6, 1972
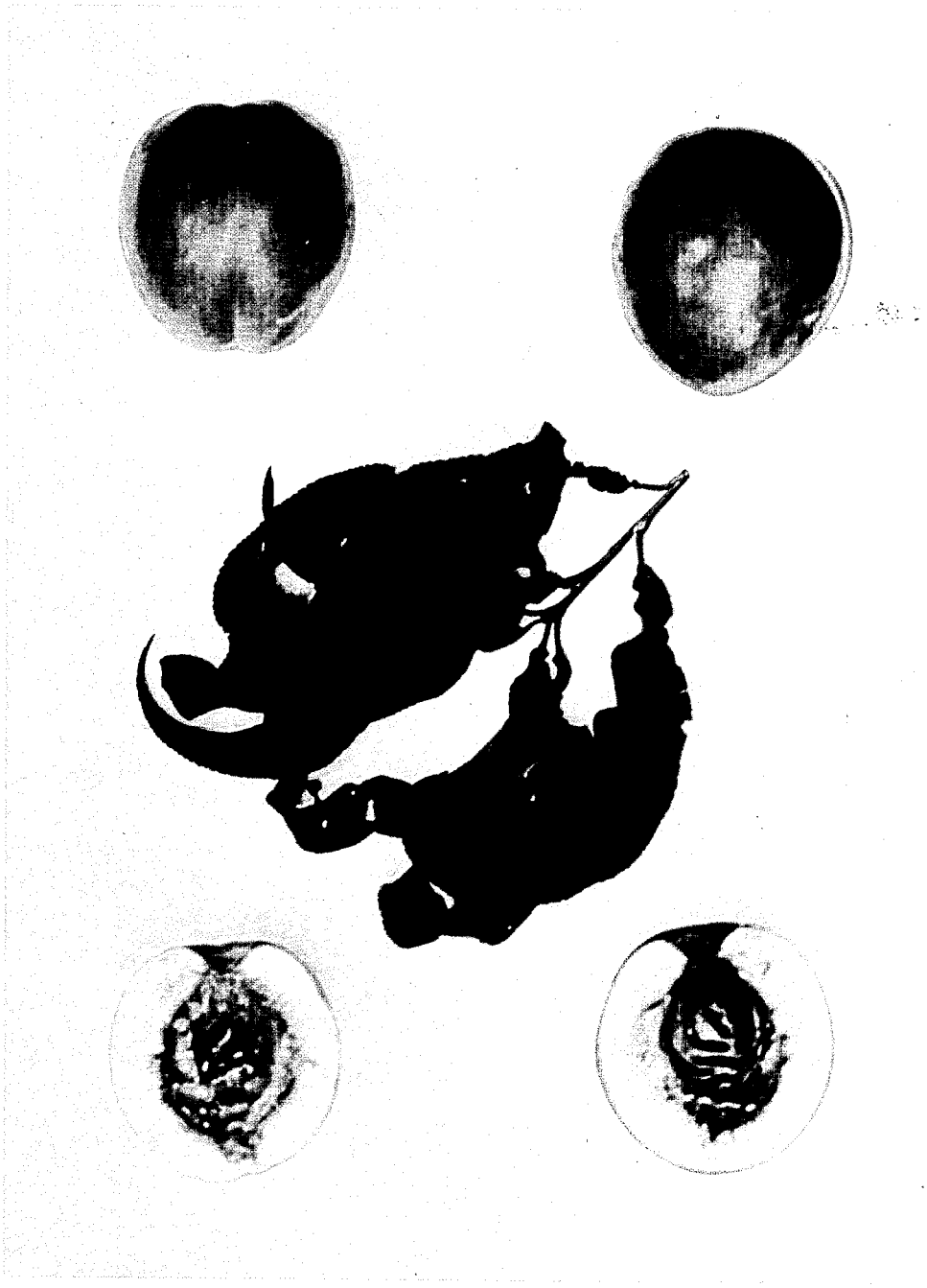

United States Patent Office

Plant Pat. 3,477
Patented Feb. 12, 1974

3,477

NECTARINE TREE

Frederic W. Anderson, Merced, Calif., assignor to Stark Bro's Nurseries and Orchards Co., Louisiana, Mo.

Filed Oct. 6, 1972, Ser. No. 295,709
Int. Cl. A01h *5/03*
U.S. Cl. Plt.—41 1 Claim

ABSTRACT OF THE DISCLOSURE

A nectarine tree which is large, vigorous, spreading, open, foliated with large to medium size lanceolate leaves having reniform glands, medium in blooming period with large, pink flowers, and a regular and productive bearer of large, globose, symmetrical, uniform fruit having orange-yellow skin substantially overspread with red shading to a deeper purplish-red, yellow flesh, and a red pit cavity with the red streaked into the flesh.

Background of the variety: Over a substanial number of years I have engaged in an extensive and continuing plant breeding program at my experimental nursery and orchard located near Le Grand, Merced County, California; one purpose of such program being to provide improved varieties of fruit trees. The present variety of nectarine tree resulted from any endeavors in the conduct of such plant breeding program.

Origin of the variety: The present variety of nectarine tree was originated by me, in my experimental nursery and orchard located as aforesaid, as a first generation ($F_1$) cross between the Red Grand nectarine (U.S. Plant Pat. No. 1,060) as the seed parent, and the Late Gold nectarine (U.S. Plant Pat. No. 2,879) as the pollen parent. In maturity, such cross evidenced certain novel and distinctive characteristics desirable for a commercially grown nectarine, and I, therefore, undertook asexual reproduction of it prepartory to ultimate commercial growing.

Asexual reproduction of the variety: I asexually reproduced the present variety of nectarine tree by top-working the same on mature orchard trees located in my said experimental orchard, and such reproductions were found to run true to the original tree in all respects.

Summary of the variety: The present variety of nectarine tree is large, vigorous, spreading, open, foliated with large to medium size lanceolate leaves having reniform glands, medium in blooming period with large, pink flowers, and a regular and productive bearer of large, globose, symmetrical, uniform fruit having orange-yellow skin substantially overspread with red shading to a deeper purplish-red, yellow flesh, and a red pit cavity with the red streaked into the flesh.

The present variety of nectarine tree, characterized as above, most nearly resembles the Late Gold, the pollen parent, but—in particular comparison thereto—the skin of the fruit has a smoother texture, a deeper red color, and less growth cracks upon ripening; the ripening period of the fruit being several days earlier than said Late Gold, and about with the Le Grand nectarine (U.S. Plant Pat. No. 549).

The present variety of nectarine tree is also characterized—in particular comparison to the Red Grand, the seed parent—by fruit which is freestone rather than clingstone, and of much better eating quality; the ripening period of the fruit being two or three days later than said Red Grand.

Brief description of the drawing: The drawing is an illustration, by photographic reproduction in color, of leaves and fruit of the variety; one fruit being cut in half to expose the flesh, with the stone remaining in place in one of the cut halves.

Description of the variety: The botanical details of this new and distinct variety of nectarine tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Density.*—Open.
- *Productivity.*—Productive.
- *Bearing.*—Regular bearer.

Trunk:
- *Size.*—Medium.
- *Texture.*—Medium.

Branches:
- *Size.*—Medium.
- *Lenticels.*—Number: Medium.

Leaves:
- *Size.*—Large to medium. Average length—4¼"–5". Average width—1⅛"–1¼".
- *Form.*—Lanceolate.
- *Thickness.*—Medium.
- *Margin.*—Crenate.
- *Petiole.*—Medium length.
- *Glands.*—Number and position—usually 2 on petiole, and 2 to 4 on blade. Medium size, reniform.
- *Color.*—Top side—Medium green (23–L–8). Under side—Lighter green (22–L–7).

Flower buds:
- *Size.*—Medium.

Flowers:
- *Blooming period.*—Medium, as compared with other varieties.
- *Date of first bloom.*—Mar. 1, 1972.
- *Date of full bloom.*—Mar. 12, 1972.
- *Size.*—Large.
- *Color.*—Pink.

Fruit:
- *Maturity when described.*—Eating ripe—July 25, 1972.
- *Date of first picking.*—July 15, 1972.
- *Date of last picking.*—July 25, 1972.
- *Size.*—Uniform, large. Average diameter axially—2⅝". Average transversely in suture plane 2¾".
- *Form.*—Uniform, symmetrical, globose.
- *Suture.*—Distinct, shallow.
- *Ventral surface.*—Rounded slightly.
- *Cavity.*—Medium depth, medium breadth.
- *Base.*—Rounded.
- *Apex.*—Short.

Skin:
- *Thickness.*—Medium.
- *Texture.*—Medium.
- *Tendency to crack.*—None.
- *Down.*—Wanting.
- *Color.*—Orange-yellow (11–L–8) overspread with red (6–L–6) shading to deep purplish-red (48–L–3) with some streaking and mottling.

Flesh:
- *Amygdalin.*—Wanting.
- *Texture.*—Very firm, crisp, melting.
- *Fibers.*—Few.
- *Ripens.*—Evenly.
- *Flavor.*—Subacid.
- *Aroma.*—Distinct to wanting.
- *Eating quality.*—Good to best.
- *Color.*—Yellow (11–L–5). Surface of pit cavity—Red (6–L–6) with the red streaked into the flesh.

Stone:
- *Type.*—Free.
- *Size.*—Medium. Average length—1¼". Average breadth—1". Average thickness—¾".

*Form.*—Oblong to oval.
*Sides.*—Equal.
*Tendency to split.*—None.
*Kernal.*—Bitter.
*Color.*—Brown (7–E–11).

Use: Market—local and long distance shiping.
Keeping quality: Very good.
Resistance to insects and diseases: No unusual susceptibilities noted.
Shipping quality: Excellent.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, spreading, open, foliated with large to medium size lanceolate leaves having reniform glands, medium in blooming period with large, pink flowers, and a regular and productive bearer of large globose, symmetrical, uniform fruit having orange-yellow skin substantially overspread with red shading to a deeper purplish-red, yellow flesh, and a red pit cavity with the red streaked into the flesh; the variety being characterized, in particular comparison to the Late Gold, by fruit which has a smoother and a deeper red skin with less growth cracks, and by fruit which ripens several days earlier than said Late Gold, and about with the Le Grand; and the variety also being characterized, in particular comparison to the Red Grand, by fruit which is freestone rather than clingstone, of better eating quality, and ripens two or three days later than said Red Grand.

No references cited.

ROBERT E. BAGWILL, Primary Examiner